United States Patent [19]

Mason et al.

[11] 4,228,081
[45] Oct. 14, 1980

[54] SEPARATION OF ISOMERS

[75] Inventors: Ronald F. Mason, Westwell; Derek A. Wood, Sittingbourne, both of England

[73] Assignee: Shell Oil Company, Houston, Tex.

[21] Appl. No.: 71,980

[22] Filed: Sep. 4, 1979

[30] Foreign Application Priority Data

Sep. 27, 1978 [GB] United Kingdom ............... 38331/78

[51] Int. Cl.$^2$ .......................................... C07D 209/52
[52] U.S. Cl. ............................................... 260/326.62
[58] Field of Search ................. 260/326.62, 326.5 SF; 562/401; 71/95

[56] References Cited

U.S. PATENT DOCUMENTS

| 3,994,942 | 11/1976 | Sherai et al. | 562/401 |
| 4,047,930 | 9/1977 | Kerr | 71/95 |

OTHER PUBLICATIONS

Achemi et al., Tet. Letters, No. 6, pp. 369–372 (1975).

*Primary Examiner*—Mary C. Lee

[57] ABSTRACT

Mixtures of the geometric isomeric forms of 3-azabicyclo-(3.1.0)hexane-2-carbonitrile are resolved by selective extraction of a mixture of their benzenesulfonic acid salts or their toluenesulfonic acid salts.

4 Claims, No Drawings

SEPARATION OF ISOMERS

BACKGROUND OF THE INVENTION

3-Azabicyclo(3.1.0)hexane-2-carboxylic acid has been found to be an effective plant male gametocide: U.S. Pat. No. 4,047,930 (the compound is designated therein as 2-carboxy-3,4-methanopyrrolidine). The compound exists in the forms of two geometric (i.e., cis, trans) isomers. Each of these isomeric forms exists in the form of optical isomers. The L,cis isomer occurs naturally in the seeds of the American horse chestnut, *Aesculus parviflora* and is active as a plant male gametocide. The racemic mixtures of both of the geometric isomeric forms are active as plant male gametocides.

3-azabicyclo(3.1.0)hexane-2-carboxylic acid can be prepared by:
(1) reducing 3-azabicyclo(3.1.0)hexan-4-one-2-carbonitrile to form 3-azabicyclo(3.1.0)hexane-2-carbonitrile;
(2) converting the 3-azabicyclo(3.1.0)hexane-2-carbonitrile to 3-azabicyclo(3.1.0)hexane-2-carboxylic acid:
  (a) by treating the nitrile with barium hydroxide to form the barium salt of the acid, then treating the salt with sulfuric acid;
  (b) by treating the nitrile with hydrochloric acid.

This process is the subject matter of applications Ser. Nos. 14,528 and 26,150. The product of the process ordinarily is a mixture of the racemates of the two geometric isomeric forms.

For various reasons, it is desirable that there be available a method for spearating one of the geometric isomeric forms from the other.

DESCRIPTION OF THE INVENTION

It has now been found that the geometric isomeric form of the acid product is essentially that of the nitrile precursor, and that the cis- and trans- isomers of 3-azabicyclo(3.1.0)hexane-2-carbonitrile can be separated with a high degree of isomeric purity from mixtures of both isomers via the corresponding benzenesulfuric acid or toluenesulfonic acid salts, as the two salts have very different solubility characteristics. This provides a method for obtaining the isolated geometric isomers of the acid.

Accordingly, the invention is a method for separating the cis- and trans-isomers of 3-azabicyclo(3.1.0)hexane-2-carbonitrile which comprises extracting a mixture of the benzenesulfonic acid or toluenesulfonic acid salts of those isomers with water, and/or methanol or ethanol, separating the resulting solution of cis-isomer salt from solid trans-isomer salt, and converting the separted salts into the corresponding nitriles.

Preferably, the acid used to form the salts is p-toluenesulfonic acid, and the solvent used to extract the salts is water.

Conversion of the isomeric nitriles into the corresponding sulfonic acid salts can be carried out under conditions which cause essentially instantaneous formation of a solid mass of mixed salts. This will normally be achieved when a mixture of the nitriles in a lower alkanol, such as methanol, ethanol or isopropyl alcohol, is treated with an equimolar proportion of the sulfonic acid in a lower alkanol. Preferably the same alkanol is used as the solvent. If necessary, solvent mixtures can also be used, e.g., mixtures of a lower alkanol and a substantial amount of a liquid alkane such as pentane, hexane or octane.

The separation of the cis- isomer from the mixture preferably is achieved by extracting the solid mass of mixed salts with water, especially with water chilled to a temperature below 5° C., or with hot ethanol.

The dissolved cis-sulfonic acid salt can be removed from the virtually undissolved trans-sulfonic acid salt by conventional methods, such as decantation or filtration.

When the formation of the sulfonic acid salts is carried out in water (or in water containing a small amount of a lower alkanol) a precipitate will normally not be formed, unless small quantities of water are used in which case the trans-isomer may crystallize at once which facilitates the separation of the isomeric salts.

In the absence of a precipitate, evaporation of the solvent(s) from the solution obtained will initially lead to the formation of solid trans-isomer (which can be isolated as such) whereas continued evaporation will lead to the formation of solid mixed salts which can then be extracted with water and/or methanol or ethanol as described hereinbelow.

It will be appreciated that a separation of the cis- and trans-isomers yielding a product of sufficiently high isomeric purity—i.e., a purity of at least 90% calculated on the amount of desired isomer present in the final product—is only achieved when both isomers present in the initial mixture are capable of forming solid crystalline salts which exhibit a marked difference in solubility characteristics. Since the benzenesulfonic acid salts and p-toluene sulfonic acid salts fulfill these two conditions, they effectively achieve the desired separation in an economically acceptable way.

The method of the present invention also has the advantage that any non-basic as well as soluble basic impurities present are discarded during the separation process, thus achieving a simultaneous chemical purification step.

The sulfonic acid salts are normally formed by adding a solution of an appropriate amount of the relevant sulfonic acid in a lower alkanol to a solution of the mixture of cis- and trans-3-azabicyclo(3.1.0)-hexane-2-carbonitrile in the same or a similar alkanol. It is then sufficient to add water, preferably iced water, to the solid mass of mixed salts isolated by, for example, decantation or filtration, and stirring the mixture obtained. It may be advantageous to apply a number of extractions until a constant cis/trans isomer ratio has been obtained. The insoluble trans-sulfonic acid salt, which normally exhibits an isomeric purity of at least 85%, and often in excess of 95%, can then be removed from the mixture, for example, by filtration, and then converted into the free trans-nitrile. Conveniently, the trans-sulfonic acid salt can also be converted directly into the corresponding free carboxylic acid, for example, by hydrolysing with a strong acid such as hydrochloric acid followed by removal of the free sulfonic acid over an ion-exchange column.

The filtrate(s) will normally contain predominantly the cis-sulfonic acid salt. Evaporation of solvent wil give solid cis-isomer salt which, like the trans-isomer salt, can be converted into the free nitrile or acid by conventional procedures.

It is to be noted that conversion of one isomeric form of the salt to the other may occur if one of the isomers, or a mixture of both, is heated in the presence of water or a lower alkanol. Thus, for example, heating of a mixture of 95% trans-isomer and 5% cis-isomer in water or a lower alkanol results in a mixture containing about two-thirds cis-isomer and one-third trans-isomer. On cooling, salt of the trans-isomer precipitates.

Conduct of the method the invention in a particular instance is described in th following example:

EXAMPLE

(a) Preparation of mixed salts

To a mixture of 33 g (0.31 mole) of cis- and trans-3-azabicyclo(3.1.0)hexane-2-carbonitrile (cis/trans ratio 62/38) in a mixture of isopropyl alcohol and hexane (50/50 w/w) was added slowly a solution of 57 g of p-toluenesulfonic acid (99% minimum purity) in 500 ml of isoprpyl alcohol while keeping the temperature at 15°-25° C. by external cooling.

The mixed salts readily crystallized. The resulting slurry was diluted with 500 ml of hexane and cooled to 0° C. The mixed salts were filtered and washed with one liter of a 50/50 (w/w) mixture of isopropyl alcohol and hexane, and then with hexane. Air dried salts weighed 72 g (0.26 mole), equivalent to 85% yield.

(b) Separation of mixed salts

The mixture obtained under (a) was slurried with de-mineralized water at 0° C. followed by filtering. 25.5 g of solid product was obtained after drying to constant weight and contained 95+% isomerically pure trans-3-azabicyclo(3.1.0)hexane-2-carbonitrile p-toluenesulfonic acid salt. This compound was characterized by comparison with a sample of trans-3-azabicyclo(3.1.0-)hexane-2-carbonitrile p-toluene sulfonic acid salt obtained from mixing a small amount of trans-3-azabicyclo(3.1.0)-hexane-2-carbonitrile in ethanol with a solution of an equimolar amount of p-toluenesulfonic acid monohydrate in ethanol. Filtration and recrystallization from methanol gave trans-3-azabicyclo(3.1.0)hexane-2-carbonitrile p-toluenesulfonic acid salt; mp: 159°-151° C. with decomposition. The alltrans structure was confirmed by derivatization gas-liquid chromatography and NMR analysis.

Concentrating the filtrate until crystals just started to separate followed by cooling in acid water and filtration gave a further 5 grams of trans-3-azabicyclo(3.1.0)hexane-2-carbonitrile p-toluenesulfonic acid salt.

The filtrate contained cis-3-azabicyclo(3.1.0)hexane-2-carbonitrile p-toluenesulfonic acid salt (cis/trans ratio 92/8), which gave, after evaporation, recrystallization from isopropyl alcohol and drying under reduced pressure, cis-3-azabicyclo(3.1.0)hexane-2-carbonitrile p-toluenesulfonic acid salt, mp: 126°-128° C. (slight decomposition). The cis/trans ratio was 99/1 (derivatization, gas liquid chromatography).

(c) Conversion of separated salts into the corresponding acids

The filtrate obtained from (b) was treated with 1500 ml of concentrated hydrochloric acid and the mixture was boiled under nitrogen. The resulting solution was stripped on a rotatory evaporator and the resulting semi-solid redissolved in 1800 ml of demineralized water.

The solution, comprising p-toluenesulfonic acid, hydrochloric acid and product, was then charged to a Dowex 50 H+ cation exchange column, which after washing through the mineral acids, released the product by elution with aqueous ammonia, from which the product was isolated by removal of water at reduced pressure and crystallization from isopropyl alcohol. After drying, the product cis-3-azabicyclo-(3.1.0)hexane-2-carboxylic acid was obtained with a water content of 10.1% and chemical purity 94+% in a cis/trans ratio 91/9 (mp: 249°-250° C. with decomposition). The chemical yield for the hydrolysis step calculates to 77% based on the starting mixed salts.

Trans-3-azabicyclo(3.1.0)hexane-2-carboxylic acid was obtained by a similar hydrolysis procedure from trans-3-azabicyclo(3.1.0)hexane-2-carbonitrile p-toluenesulfonic acid salt. The product obtained contained less than 1% by weight of water and its isomeric purity exceeded 95%. The chemical yield was 82% (mp: 260°-262° C. with decomposition).

We claim:

1. A method for separating the cis- and trans- isomeric forms of 3-azabicyclo(3.1.0)hexane-2-carbonitrile from mixtures thereof which comprises extracting a mixture of the benzenesulfonic acid or toluenesulfonic acid salts of the isomers with a solvent selected from one or more of water, methanol and ethanol, recovering separately the salts in the extract and the extracted solid phase.

2. A method according to claim 1 wherein the salts of the isomeric forms in the salts of p-toluenesulfonic acid, the extracting solvent is water and the extraction is carried out at a temperature below about 5° C.

3. A salt selected from the benzenesulfonic acid and toluenesulfonic acid salts of 3-azabicyclo(3.1.0)hexane-2-carbonitrile.

4. A salt according to claim 3 wherein the toluenesulfonic acid is para-toluenesulfonic acid.

* * * * *